(12) United States Patent
Guo

(10) Patent No.: US 11,254,915 B2
(45) Date of Patent: *Feb. 22, 2022

(54) METHOD FOR SEPARATING AND CULTURING MESENCHYMAL STEM CELLS FROM WHARTON'S JELLY TISSUE OF UMBILICAL CORD

(71) Applicants: Lei Guo, Beijing (CN); Cheng Li, Beijing (CN)

(72) Inventor: Lei Guo, Beijing (CN)

(73) Assignees: Lei Guo, Beijing (CN); Cheng Li, Beijing (CN)

( * ) Notice: Subject to any disclaimer, the term of this patent is extended or adjusted under 35 U.S.C. 154(b) by 638 days.

This patent is subject to a terminal disclaimer.

(21) Appl. No.: 16/061,304

(22) PCT Filed: Dec. 11, 2015

(86) PCT No.: PCT/CN2015/097126
§ 371 (c)(1),
(2) Date: Jun. 11, 2018

(87) PCT Pub. No.: WO2017/096611
PCT Pub. Date: Jun. 15, 2017

(65) Prior Publication Data
US 2020/0165571 A1    May 28, 2020

(51) Int. Cl.
*C12N 5/0775* (2010.01)
*C12N 5/00* (2006.01)

(52) U.S. Cl.
CPC ......... *C12N 5/0665* (2013.01); *C12N 5/0031* (2013.01); *C12N 5/0668* (2013.01); *C12N 2500/24* (2013.01); *C12N 2500/32* (2013.01); *C12N 2500/44* (2013.01); *C12N 2500/60* (2013.01); *C12N 2500/90* (2013.01); *C12N 2501/115* (2013.01)

(58) Field of Classification Search
None
See application file for complete search history.

(56) References Cited

U.S. PATENT DOCUMENTS

| | | | |
|---|---|---|---|
| 6,372,494 | B1 | 4/2002 | Naughton et al. |
| 11,091,739 | B2 | 8/2021 | Guo |
| 11,098,280 | B2 | 8/2021 | Guo |
| 2005/0169935 | A1* | 8/2005 | Aylsworth ............ A61K 39/39 424/185.1 |
| 2008/0118477 | A1* | 5/2008 | Christopherson .... C12N 5/0647 424/93.7 |
| 2010/0167328 | A1* | 7/2010 | Avent .................. G01N 33/6893 435/25 |
| 2013/0005026 | A1* | 1/2013 | Gombrich ........ G01N 33/57411 435/287.2 |
| 2013/0251684 | A1 | 9/2013 | Tseng et al. |
| 2013/0302285 | A1 | 11/2013 | Fong et al. |

FOREIGN PATENT DOCUMENTS

| | | | |
|---|---|---|---|
| CN | 102559590 A | 7/2012 | |
| CN | 103805562 A | 5/2014 | |
| CN | 104736160 A | 6/2015 | |
| CN | 105420187 B | 6/2019 | |
| CN | 105420188 B | 6/2019 | |
| WO | WO 09/044379 | * 4/2009 | ............... C12N 5/08 |
| WO | 2012018307 A1 | 2/2012 | |
| WO | WO 2012/148125 A1 | 11/2012 | |
| WO | 2013086436 A1 | 6/2013 | |
| WO | 2013173376 A1 | 11/2013 | |
| WO | WO 2017/096616 A1 | 6/2017 | |
| WO | WO 2017/096617 A1 | 6/2017 | |

OTHER PUBLICATIONS

Extended European Search Report dated Jun. 28, 2019, for corresponding EP Application No. 15910085.8 (7 pages).
Kim, et al., "Human chorionic-plate-derived mesenchymal stem cells and Wharton's jelly-derived mesenchymal stem cells: a comparative analysis of their potential as placenta-derived stem cells", Cell and Tissue Research (2011), vol. 346, No. 1, pp. 53-64.
International Search Report dated Sep. 14, 2016 for corresponding PCT Application No. PCT/CN2015/097126, with English translation (6 pages).
Machine English translation of CN 103805562 A (1 page).
Sabapathy, et al., "Human Wharton's Jelly Mesenchymal Stem Cells Plasticity Augments Scar-Free Skin Wound Healing with Hair Growth," PLOS One, vol. 9, No. 4, Apr. 15, 2014, pp. 1-10.
U.S. Restriction Requirement dated Jun. 15, 2020, for cross reference U.S. Appl. No. 16/061,232, (8 pages).
U.S. Restriction Requirement dated Jun. 16, 2020, for cross reference U.S. Appl. No. 16/061,272, (7 pages).
U.S. Office action dated Sep. 16, 2020, for cross reference U.S. Appl. No. 16/061,232, (16 pages).
U.S. Office action dated Sep. 16, 2020, for cross reference U.S. Appl. No. 16/061,272, (14 pages).
U.S. Office action dated Feb. 5, 2021, for cross reference U.S. Appl. No. 16/061,232, (14 pages).
U.S. Office action dated Feb. 9, 2021, for cross reference U.S. Appl. No. 16/061,272, (7 pages).
U.S. Notice of Allowance and Notice of Allowability dated May 19, 2021, for cross reference U.S. Appl. No. 16/061,232, (10 pages).
U.S. Notice of Allowance and Notice of Allowability dated Jun. 25, 2021, for cross reference U.S. Appl. No. 16/061,272, (10 pages).

(Continued)

*Primary Examiner* — Allison M Fox
(74) *Attorney, Agent, or Firm* — Lewis Roca Rothgerber Christie LLP

(57) ABSTRACT

Provided is a method for separating and extracting mesenchymal stem cells from the human umbilical cord. The method uses healthy neonatal umbilical cord tissue; after cleaning and disinfection, mechanically pulverising same, separating the Wharton's jelly, and after treating with erythrocyte lysate, carrying out suspension culture in a serum-free culture medium. Replacing the liquid every 3-5 days; after the plate adherence rate reaches 30-70%, carrying out trypsin digestion, and then collecting the cells by centrifugation for passage amplification, until the rate of confluence of the cells reaches 80-90% confluence, thereby obtaining high purity umbilical cord mesenchymal stem cells.

18 Claims, 9 Drawing Sheets

(56) References Cited

OTHER PUBLICATIONS

International Search Report of Corresponding International Application No. PCT/CN2015/097148 dated Sep. 14, 2016, with English translation (6 pages).
Written Opinion of the International Searching Authority of Corresponding International Application No. PCT/CN2015/097148 dated Sep. 14, 2016, with English translation (12 pages).
Written Opinion of the International Searching Authority of Corresponding International Application No. PCT/CN2015/097150 dated Sep. 20, 2016, with English translation, (15 pages).
11140-MEM non-essential amino acids. Technical Resources. ThermoFisher Scientific, p. 1 (Year: 2015).
Chen et al., Human Umbilical Cord-Derived Mesenchymal Stem Cells Do Not Undergo Malignant Transformation during Long-Term Culturing in Serum-Free Medium, 2015, pp. 1-8, vol. 9, No. 6, PLOS One.
Furue et al., Heparin promotes the growth of human embryonic stem cells in a defined serum-free medium, Sep. 9, 2008, pp. 13409-13414, vol. 105, No. 36, The National Academy of Sciences of the USA.
Jung et al., Ex Vivo Expansion of Human Mesenchymal Stem Cells in Defined Serum-Free Media, Review Article, 2012, pp. 1-21, Stem Cells International.
Leng et al., Molecular imaging for assessment of mesenchymal stem cells mediated breast cancer therapy, Biomaterials, Author Manuscript, Jun. 2014, pp. 1-18, vol. 35, No. 19, Elsevier Ltd.
Montes et al., Feeder-free maintenance of hESCs in mesenchymal stem cell-conditioned media: distinct requirements forTGF-β and IGF-II, Cell Research, Jun. 2009, pp. 698-709, vol. 19, No. 6.
Rajala et al., Testing of nine different xeno-free culture media for human embryonic stem cell cultures, Human Reproduction, 2007, pp. 1231-1238, vol. 22, No. 5, Oxford University Press on behalf of the European Society of Human reproduction and Embryology.
Wang et al., Sustaining effect of cultured adult marrow mesenchymal stem cells supernatant on culture and proliferation of mesenchymal stem cells from human umbilical cord blood in vitro, Med. J. NDFNC, 2006, pp. 447-449, vol. 27, No. 6, with English Translation (2 pages).
Xiao et al., Differentiation of Schwann-like cells from human umbilical cord blood mesenchymal stem cells in vitro, 2015, pp. 1146-1152, vol. 11, Molecular Medicine Reports.
Yang et al., Conditioned Media from Human Adipose Tissue-Derived Mesenchymal Stem Cells and Umbilical Cord-Derived Mesenchymal Stem Cells Efficiently Induced the Apoptosis and Differentiation in Human Glioma Cell Lines In Vitro, Research Article, BioMed Research International, 2014, pp. 1-13, Article ID 109389, Hindawi Publishing Corporation.
Zhao et al., Sustaining effect of cultured adult adipose tissue-derived mesenchymal stem cells supernatant on culture and proliferation of mesenchymal stem cells from human umbilical cord blood in vitro, Journal of Mudanjiang Medical University, 2010, pp. 14-16, vol. 31, No. 4, with English Translation (1 page).
Zhao et al., Differences of human umbilical cord blood-derived mesenchymal stems cells cultured in different media, Chinese Journal of Tissue Engineering research, May 7, 2013, pp. 3449-3454, vol. 17, No. 19, with English Translation (3 pages).
Machine English translation of CN 102559590 A (9 pages).
Machine English translation of CN 105420187 B (8 pages).
Machine English translation of CN 105420188 B (8 pages).
Machine English translation of WO 2012/148125 A1 (8 pages).
Machine English translation of WO 2017/096616 A1 (9 pages).
Machine English translation of WO 2017/096617 A1 (9 pages).

* cited by examiner

FIG. 1
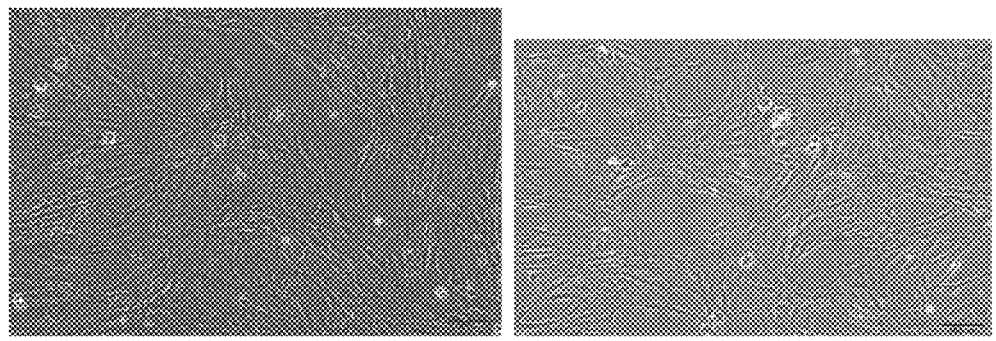
FIG. 1A    FIG. 1B
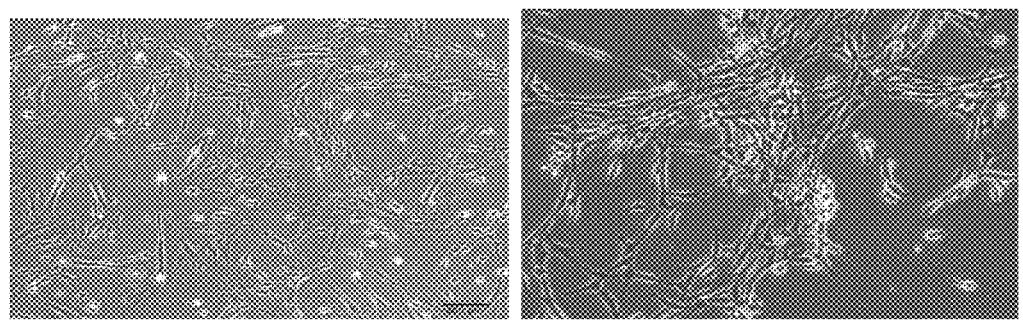
FIG. 1C    FIG. 1D
FIG. 2
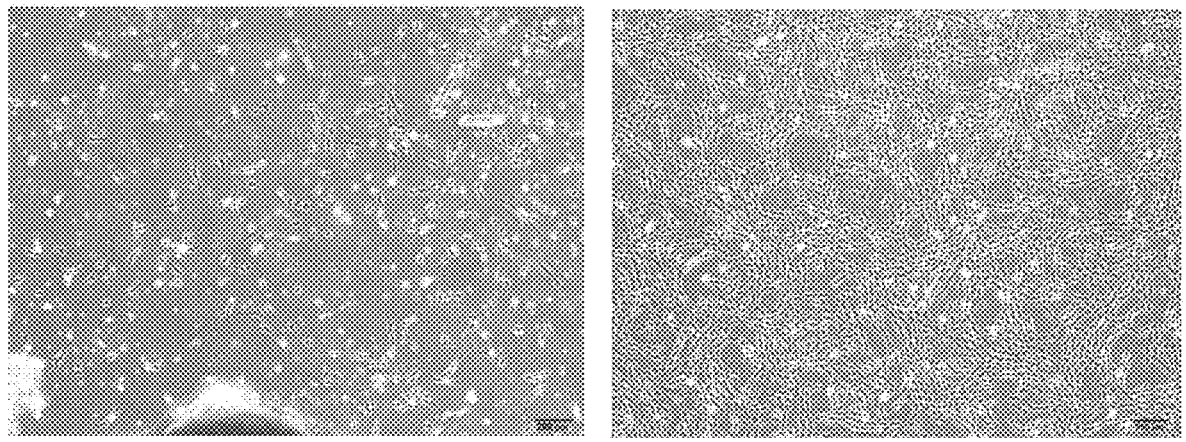
FIG. 2A    FIG. 2B

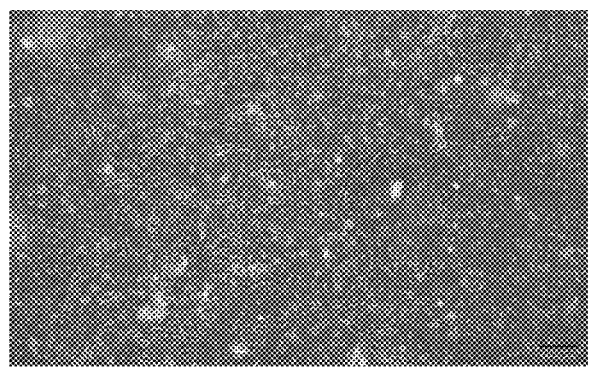
FIG. 2C
FIG. 3
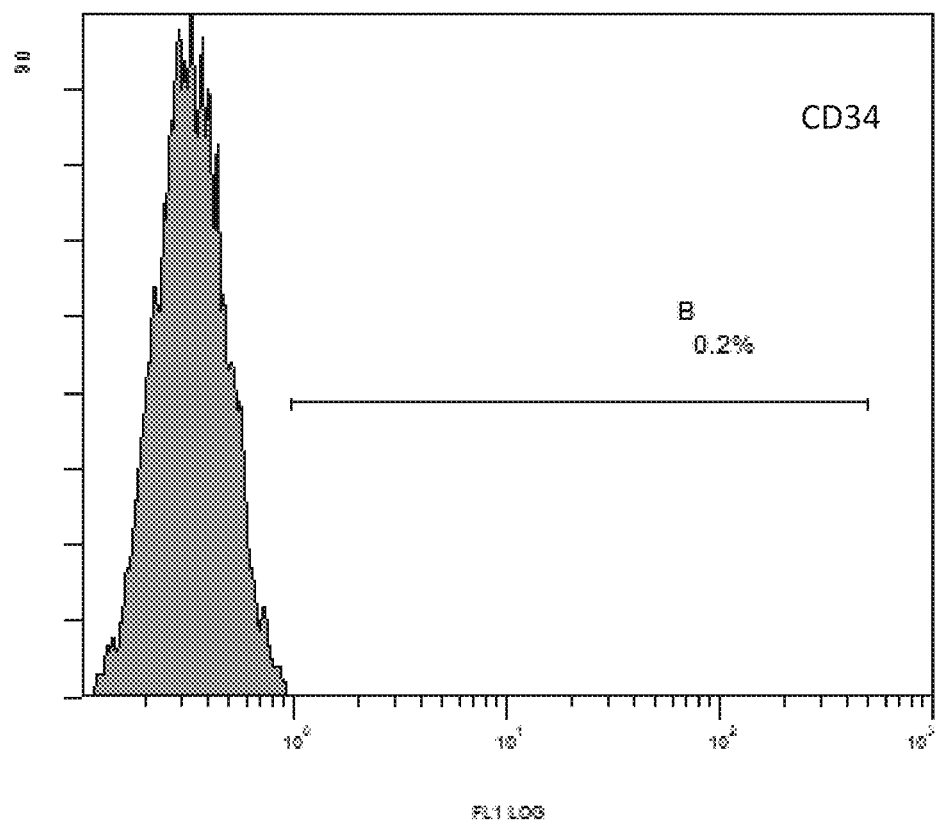
FIG. 3A

FIG. 4
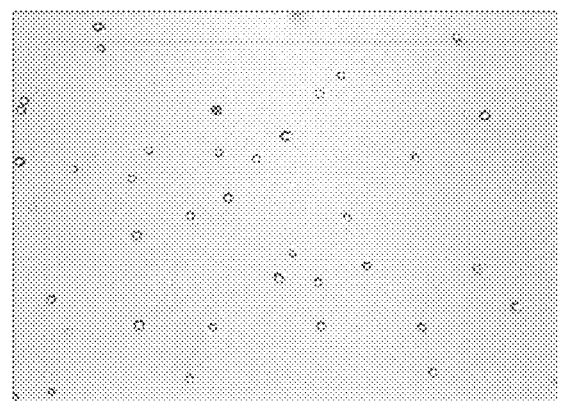
FIG. 4A
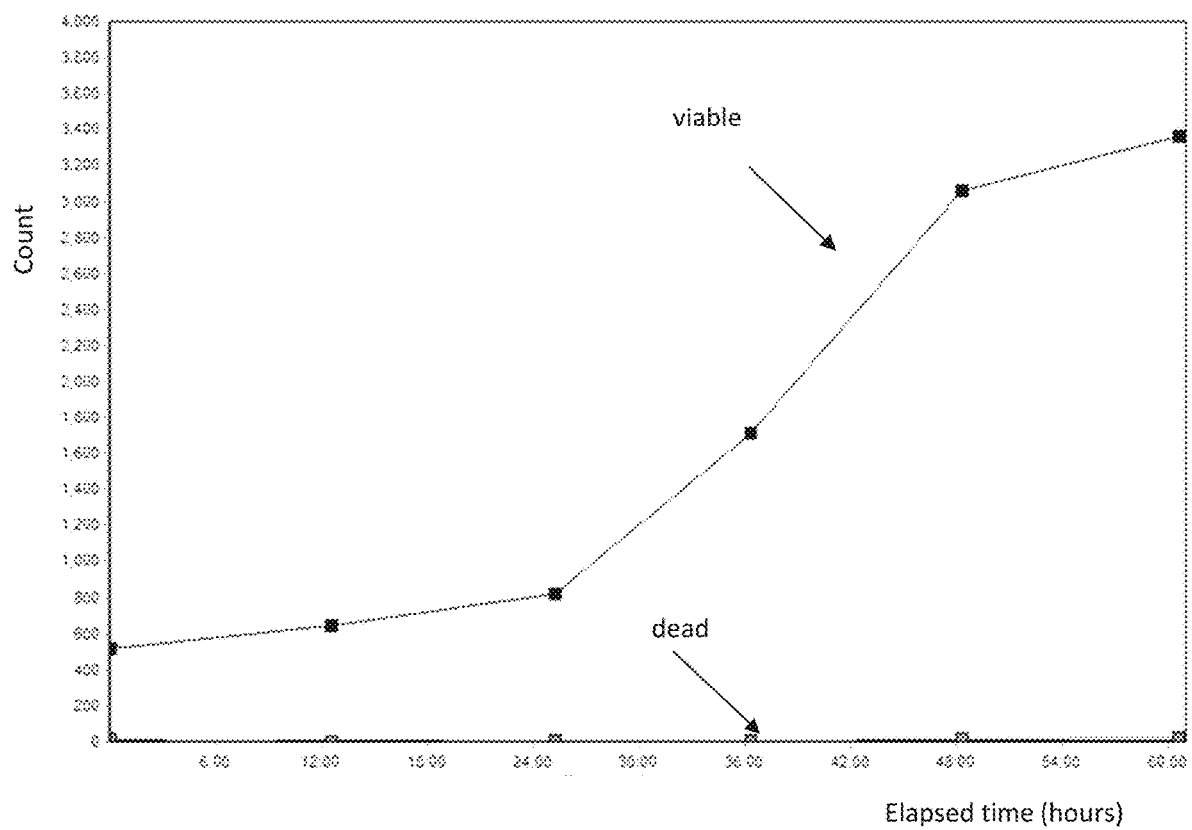
FIG. 4B

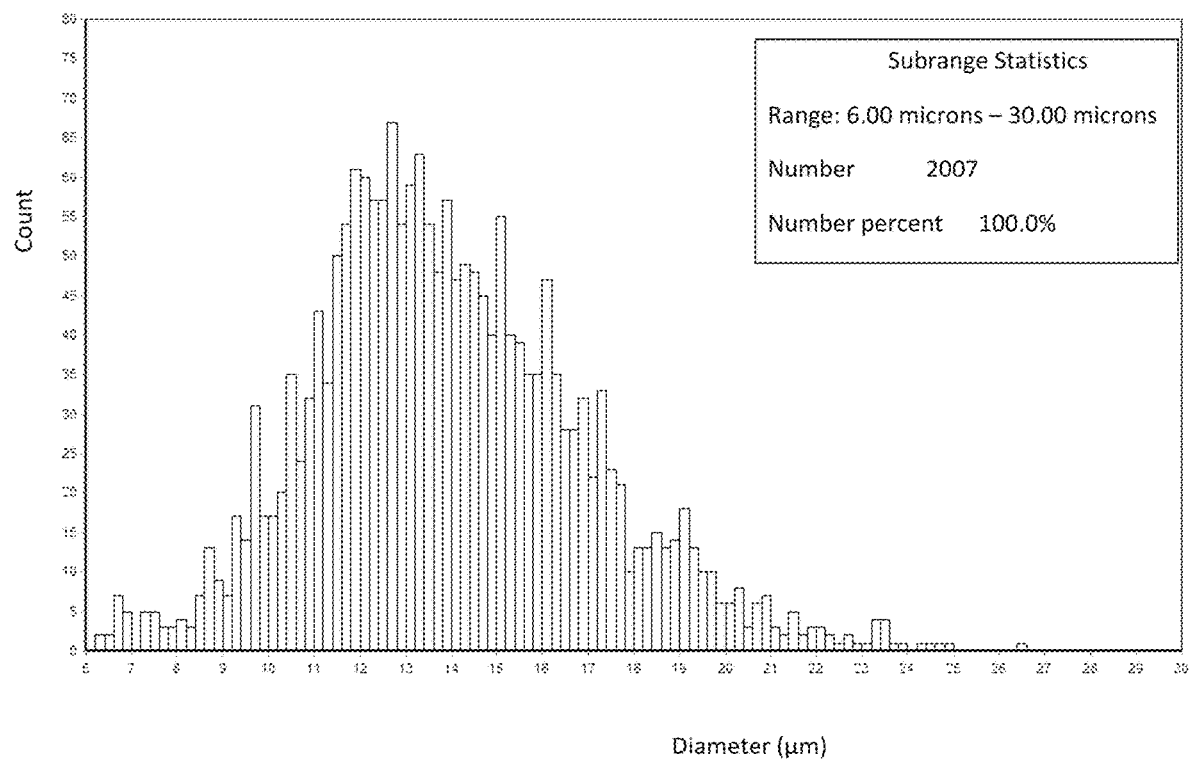
FIG. 4C
FIG. 5
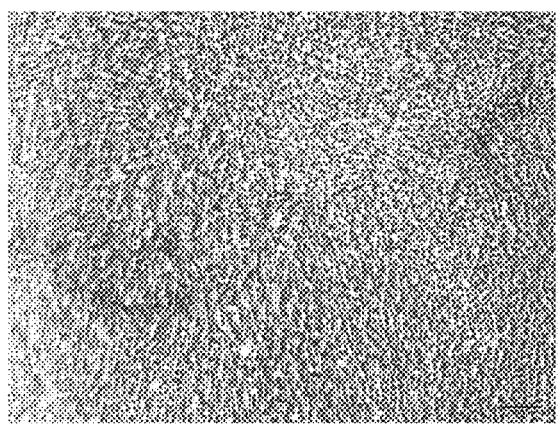
FIG. 5A
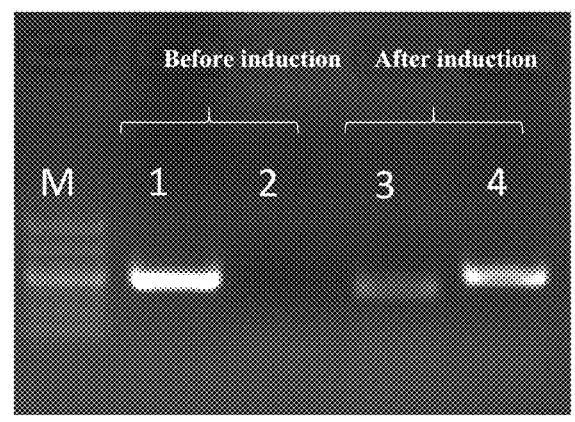
FIG. 5B

FIG. 6
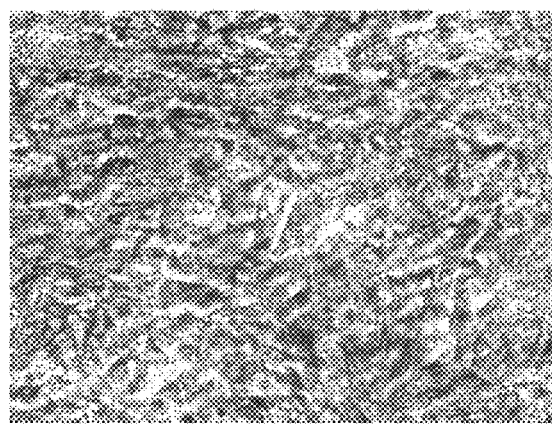
FIG. 6A
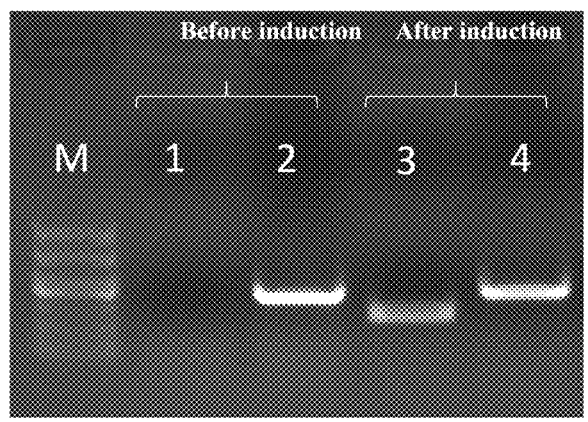
FIG. 6B
FIG. 7
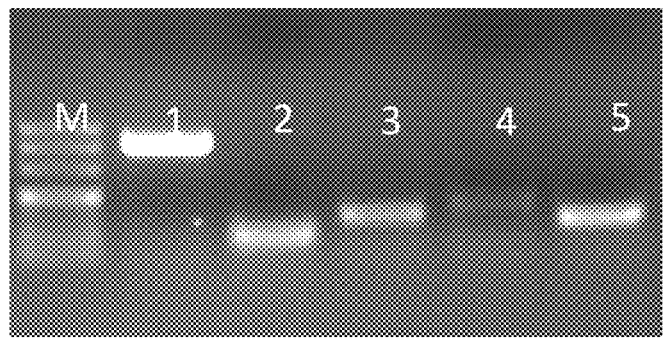

METHOD FOR SEPARATING AND CULTURING MESENCHYMAL STEM CELLS FROM WHARTON'S JELLY TISSUE OF UMBILICAL CORD

CROSS-REFERENCE TO RELATED APPLICATION(S)

This application is a National Phase Patent Application and claims priority to and the benefit of International Application Number PCT/CN2015/097126, filed on Dec. 11, 2015, the entire contents of which are incorporated herein by reference.

TECHNICAL FIELD

The invention relates to a stable method for separating and extracting mesenchymal stem cells from umbilical cord, especially a method for separating and culturing mesenchymal stem cells from Wharton's jelly tissue of umbilical cord.

BACKGROUND OF THE INVENTION

Mesenchymal stem cell (MSC) is an important member of stem cell family, which derives from the mesoderm and ectoderm of early development stage and exists in the connective tissues and mesenchymes in organs of the whole body. MSC was found in bone marrow for the first time in the late 1970s; however, until the 90s of last century, only when the multiple differentiation potential of MSC was recognized, such a stem cell began to draw more and more attention.

Mesenchymal stem cell belongs to pluripotent stem cells. At present, previous study has shown that MSCs can be induced to differentiate into many types of tissue cells and the like cells, such as fat cells, bone cells, bone ligament cells, nerve cells, liver cells, myocardium cells, endothelium cells, islet cells and so on. And it has also been found that mesenchymal stem cells have significant effects, for example on immunosuppression, regulation of endocrine system, modulation of nervous system and improvement in cardiovascular function.

By now, the extraction of mesenchymal stem cells from various tissues and organs has been widely studied, including from fat, bone marrow, amniotic fluid, placenta, umbilical cord, cord blood, and periodontium. The mesenchymal stem cells from umbilical cord, which are available in high purity and large quantity because of the simple growth environment and convenient extraction in vitro, may become an ideal substitute for mesenchymal stem cells of bone marrow, and have a wider potential of clinical application.

In view of the multi-directional differentiation potential of cord pluripotent stem cells and the potential of application in the field of disease treatment, there will be a broad prospect in the business of cord mesenchymal stem cells storage in the domestic market. Therefore, how to guarantee an efficient and standard rate of separating and extracting stem cells, and ensure the quality of stem cells so as to meet the future clinical need for stem cell transplantation is an urgent problem to be solved in stem cell storage in China.

Currently, most of cord mesenchymal stem cells are prepared by enzyme digestion and tissue adherence method. However, during separation and extraction, the interference from red blood cells is an important factor affecting the quality and quantity of cord mesenchymal stem cells. The existence of a large number of red blood cells limits the growth space of mesenchymal stem cells, and affects viability of the stem cells, thereby having a great influence on the separation, extraction, exploitation and utilization of cord mesenchymal stem cells.

SUMMARY OF THE INVENTION

Therefore, the purpose of the invention is to provide an improved method for separating and extracting umbilical cord mesenchymal stem cells to overcome the interference from red blood cells, so as to meet the needs in this field.

Another purpose of the invention is to provide umbilical cord mesenchymal stem cells obtained by the method of the present invention.

Specifically, in view of the present situation of extracting human umbilical cord mesenchymal stem cells at home and abroad, the present invention employs red blood cell lysis buffer and suspension culture to separate primary mesenchymal stem cells from fresh Wharton's jelly tissue of umbilical cord, and employs serum-free culture system for primary culture and stable passage, thereby increasing the rate of successful separation and extraction and improving the purity of umbilical cord mesenchymal stem cells, and making the clinical application of human umbilical cord mesenchymal stem cells possible.

Technical solutions of the invention are as follows.

In one aspect, the present invention provides a method for separating and extracting mesenchymal stem cells from freshly isolated Wharton's jelly tissue of umbilical cord, which is a method for separating and culturing umbilical cord mesenchymal stem cells, the method comprising: using a red blood cell lysis buffer to treat the Wharton's jelly tissue separated from umbilical cord, and using a serum-free medium for mesenchymal stem cells for culture.

The red blood cell lysis buffer used in the present invention is an aqueous solution comprising $NH_4Cl$ and $Na_2$-EDTA, preferably an aqueous solution comprising 1-20 g/L $NH_4Cl$ and 0.05-0.2 mM $Na_2$-EDTA, more preferably an aqueous solution comprising 5-10 g/L $NH_4Cl$ and 0.1 mM $Na_2$-EDTA, pH 7.2-7.4. Before use, the red blood cell lysis buffer is filtered through 0.22 μm microfiltration membrane and equilibrated to room temperature.

The serum-free medium for mesenchymal stem cells used in the present invention comprises a-MEM/DMEM-F12, β-mercapto ethanol, non-essential amino acids, recombinant human basic fibroblast growth factor (b-FGF) and serum substitute.

Preferably, the serum-free medium for mesenchymal stem cells comprises 0.05-0.2 parts by volume of β-mercapto ethanol, 0.5-2 parts by volume of an aqueous solution of non-essential amino acids, 8-12 parts by volume of serum substitute, 85-95 parts by volume of a-MEM/DMEM-F12 and recombinant human basic fibroblast growth factor at a final concentration of 5-15 ng/ml, wherein the aqueous solution of non-essential amino acids comprises glycine, alanine, L-asparagine, L-aspartic acid, glutamic acid, proline and serine each at a concentration of 8-12 mM; more preferably, the serum-free medium for mesenchymal stem cells comprises 0.1 parts by volume of β-mercapto ethanol, 1 part by volume of the aqueous solution of non-essential amino acids, 10 parts by volume of the serum substitute, 89 parts by volume of a-MEM/DMEM-F12 and the recombinant human basic fibroblast growth factor at a final concentration of 10 ng/ml; most preferably, the serum-free medium for mesenchymal stem cells consists of a-MEM/DMEM-F12, β-mercapto ethanol, the aqueous solution of non-essential amino acids, the recombinant human basic fibroblast growth factor and the serum substitute.

According to particular embodiments of the present application, the product available from Gibco under Catalog No. 11140 can be used as the aqueous solution of non-essential amino acids.

According to particular embodiments of the present application, the KnockOut™ Serum Replacement available from Gibco under Catalog No. 10828-010 can be used as the serum substitute.

The method of the present invention specifically comprises: cutting the obtained Wharton's jelly tissue into tissue blocks, adding the red blood cell lysis buffer with a volume of 1-3 times the volume of the tissue blocks, and treating the tissue blocks with the buffer at room temperature for 2-5 minutes; and, culturing the obtained tissue with the serum-free medium for mesenchymal stem cells to obtain primary mesenchymal stem cells.

Preferably, the method comprises the following steps: cutting washed Wharton's jelly tissue of umbilical cord into tissue blocks each in size of 1-3 mm$^3$, adding the red blood cell lysis buffer with a volume of 1.5-2 times the volume of the tissue blocks, and treating the tissue blocks with the buffer at room temperature for 2-5 minutes; and, plating the obtained tissue blocks evenly on a culture dish to reach a coverage of 60-80%, and adding the serum-free medium for mesenchymal stem cells with a volume of 3-5 times the volume of the tissue blocks, then culturing at 37° C., 5% $CO_2$, during which replacing half the medium with fresh medium at 3-5 days, and removing the tissue blocks when cells have uniformly grown out of the bottom of the tissue blocks at 5-15 days; and, replacing the medium in entirety with fresh serum-free medium for mesenchymal stem cells for further culture during which the medium is replaced with fresh medium every 3-4 days.

Preferably, the method comprises the following steps:

(1) Pretreatment of Umbilical Cord Tissue:

Cutting fresh umbilical cord into segments, removing intravascular blood, longitudinally cutting each segment, eliminating umbilical artery and umbilical vein, bluntly dissecting the Wharton's jelly tissue and washing the same with PBS;

(2) Treatment with the Red Blood Cell Lysis Buffer:

Cutting the Wharton's jelly tissue obtained by step (1) into tissue blocks, adding the red blood cell lysis buffer to treat the tissue blocks, collecting the treated tissue blocks by centrifugation, and washing them with PBS;

(3) Primary Culture:

Culturing the tissue blocks obtained by step (2) in the serum-free medium for mesenchymal stem cells to obtain primary mesenchymal stem cells.

Preferably, the method further comprises the following steps:

(4) Supernatant Detection:

Taking the supernatant of cell culture obtained by step (3) and detecting one or more selected from the group consisting of hepatitis A, hepatitis B, hepatitis C, syphilis, human immunodeficiency virus, *mycoplasma, chlamydia* and endotoxin;

(5) Passage Culture:

Selecting the cultured cells with negative results in step (4), collecting cells by centrifugation after trypsin digestion, passage culturing, and collecting the cells for reserving, or freezing conservation or continuing passage culture;

(6) Cell Detection:

Taking the cells cultured in step (5), and detecting one or more selected from the group consisting of differentiation, cell activity, cell purity, cell contamination and proliferation profile.

Preferably, the step (1) includes: cutting the fresh umbilical cord into segments each of 2-3 cm in length, removing the intravascular blood, longitudinally cutting each segment, eliminating the umbilical artery and the umbilical vein, bluntly dissecting the Wharton's jelly tissue, adding PBS with a volume of 2-5 times the volume of the tissue, and washing the tissue by shaking slightly.

Preferably, the Step (2) Includes:

Cutting the washed Wharton's jelly tissue into tissue blocks each in size of 1-3 mm$^3$, adding the red blood cell lysis buffer with a volume of 1.5-2 times the volume of the tissue blocks, treating the tissue blocks with the buffer at room temperature for 2-5 minutes, collecting the treated tissue blocks by centrifugation, and washing 2-3 times with PBS; wherein the centrifugation preferably is performed at 1000-1200 rpm, 4° C. for 6 minutes.

Preferably, the Step (3) Includes:

Plating the tissue blocks obtained by step (2) evenly on a culture dish to reach a coverage of 60-80%, preferably 70%, adding the serum-free medium for mesenchymal stem cells with a volume of 3-5 times the volume of the tissue blocks, then culturing at 37° C., 5% $CO_2$, during which replacing half the medium with fresh medium at 3-5 days, and removing the tissue blocks when cells have evenly grown out of the bottom of the tissue blocks at 5-15 days, preferably at 7-10 days; and, replacing the medium in entirety with fresh serum-free medium for mesenchymal stem cells for further culture during which the medium is replaced with fresh medium every 3-4 days.

Preferably, the Step (4) Includes:

Taking the supernatant of cell culture obtained by step (3) and detecting all of the followings: hepatitis A, hepatitis B, hepatitis C, syphilis, human immunodeficiency virus, *mycoplasma, chlamydia* and endotoxin.

Preferably, the Step (5) Includes:

Selecting the cultured cells with all negative results in step (4), performing trypsin digestion at 30-80%, preferably 40-50% confluence, collecting cells by centrifugation, passage culturing the cells in serum-free medium for mesenchymal stem cells to reach 50-90%, preferably 80-90% confluence, and collecting the cells for reserving or freezing conservation, or continuing passage culture; wherein preferably, the trypsin is used at a mass percent concentration of 0.125%, and the digestion is performed for 1-2 minutes while patting the side walls of culture dish or culture flask used; and wherein preferably, the centrifugation is performed at 1000-1200 rpm, 4° C. for 6 minutes.

Preferably, the collected cells are freezing conserved in liquid nitrogen at −196° C. at a density of 2-3×10$^6$ cells/ml; or preferably, the collected cells are passage cultured in a rate of 1:3-1:4.

Preferably, the Step (6) Includes:

Taking the cells cultured in step (5), and detecting all of the followings: differentiation, cell activity, cell purity, cell contamination and proliferation profile.

Preferably, prior to the step (1), the method further comprises washing, preserving and pre-processing the umbilical cord, preferably comprising:

collecting aseptically umbilical cord tissue from a healthy newborn by natural or cesarean section delivery, putting the umbilical cord tissue into preservation and transportion solution for umbilical cord after surface washing with sterile saline, preferably transporting the umbilical cord in ice to a clean cell laboratory within 6 hours; and before use, washing the fresh umbilical cord 2-3 times with 75% aqueous ethanol, then 3-5 times with sterile saline.

Preferably, the preservation and transportion solution for umbilical cord is magnesium and calcium free D-Hank's comprising penicillin sodium, streptomycin sulfate, gentamicin and amphotericin B for injection; more preferably, the concentration of each of penicillin sodium, streptomycin sulfate and gentamicin is 100-200 U/ml, preferably 150 U/ml, and the concentration of amphotericin B is 200-400 U/ml, preferably 300 U/ml.

According to particular embodiments of the present invention, the method for separating and extracting mesenchymal stem cells from freshly isolated umbilical cord tissue comprises the following steps:

(1) collecting and transporting the sample: collecting aseptically umbilical cord tissue sample from a healthy neoborn by natural or cesarean section delivery, putting the sample into the preservation and transportation solution for umbilical cord, and transporting in ice;

(2) Washing and sterilizing the umbilical cord sample: putting the fresh umbilical cord sample into a 50 ml aseptic centrifuge tube, washing the sample 2-3 times with 75% aqueous ethanol, then 3-5 times with sterile saline;

(3) Pre-processing the umbilical cord sample: cutting the umbilical cord into segments each of 2-3 cm in length with ophthalmic scissors, removing the intravascular blood with tweezers, longitudinally cutting each segment, eliminating two umbilical arteries and one umbilical vein with hemostatic forceps, bluntly dissecting the Wharton's jelly tissue and putting it into a 50 ml centrifuge tube, adding PBS with a volume of 2-5 times the volume of the tissue, and washing the tissue by shaking slightly;

(4) Treating with the red blood cell lysis buffer: transferring the Wharton's jelly tissue to a clean and sterile 100 mm culture dish, cutting the tissue into tissue blocks each in size of 1-3 mm$^3$; transferring minced cord tissue into a centrifuge tube, adding the red blood cell lysis buffer with a volume of 1.5-2 times the volume of the tissue blocks; treating the tissue blocks with the buffer at room temperature for 2 minutes, collecting the treated tissue blocks by centrifugation; and washing 2-3 times with PBS;

(5) Primary Culture:

Plating the tissue blocks of Wharton's jelly tissue evenly on a 100 mm culture dish to reach a coverage of 70%, adding 10 ml of the serum-free medium for mesenchymal stem cells, then culturing in an incubator at 37° C., 5% $CO_2$, during which removing the dish out of the incubator and replacing half the medium with fresh medium at 3-5 days for further culture; and removing the tissue blocks when cells have uniformly grown out of the bottom of the tissue blocks at 7-10 days, and replacing the medium in entirety with fresh medium for further culture during which the medium is replaced with fresh medium every 3 days;

(6) Taking the supernatant of cell culture obtained by step (5) and detecting all of the followings: hepatitis A, hepatitis B, hepatitis C, syphilis, human immunodeficiency virus, *mycoplasma, chlamydia* and endotoxin;

(7) Passage culturing: performing trypsin digestion at about 30-70% confluence in the dish, collecting cells by centrifugation and discarding the supernatant, re-inoculating the cells to a cell culture flask for further passage culture to reach 80-90% confluence, and collecting the cells for reserving or freezing conservation, or continuing passage culture;

(8) Detecting all of the followings of the mesenchymal stem cells obtained by step (7): differentiation, cell activity, cell purity, cell contamination and proliferation profile.

In the methods mentioned above, the sample is fresh umbilical cord tissue.

In the methods mentioned above, the medium for the mesenchymal stem cells is serum-free medium, which comprises 0.1 parts by volume of β-mercapto ethanol, 1 part by volume of the aqueous solution of non-essential amino acids, 10 parts by volume of serum substitute, 89 parts by volume of a-MEM/DMEM-F12 and b-FGF at a final concentration of 10 ng/ml.

The red blood cell lysis buffer is an aqueous solution comprising 5-20 g/L $NH_4Cl$ and 0.1 mmol/L $Na_2$-EDTA, pH 7.2-7.4, which is filtered through 0.22 μm microfiltration membrane and equilibrated to room temperature before use.

And in step (7), the trypsin has a concentration of 0.125%, and the digestion is performed for 1-2 minutes while patting the side walls of culture dishe or culture flask used.

In another aspect, the present invention further provides the mesenchymal stem cells prepared by the methods mentioned above.

Preferably, the mesenchymal stem cells have characteristics as follows:

(1) Adhering to plastic container(s), appearing as spindle-shape and growing in whorls;

(2) Ratio of CD29, CD44, CD73, CD90, CD105 or HLA-ABC positive cells greater than 99%; and ratio of CD45, CD34 or HLA-DR positive cells less than 1.0%;

(3) Capable of being induced to differentiate into osteogenic cells and adipogenic cells in vitro;

(4) Ratio of viable cells detected above 99%;

(5) Having a typical "S type" growth curve; and (6) Expressing pluripotency genes which are one or more selected from the group consisting of SSEA-4, OCT-4, NANOG and SOX-2.

In a further aspect, the present invention provides the use of the red blood cell lysis buffer and/or the serum-free medium for mesenchymal stem cells in the preparation of an agent for separating and culturing mesenchymal stem cells.

In a yet another aspect, the present invention provides a kit for separating and culturing mesenchymal stem cells, which comprises the red blood cell lysis buffer and/or the serum-free medium for mesenchymal stem cells of the present invention.

Cell viability is the most important quality index for controlling mesenchymal stem cells. However, during separation and extraction of the umbilical cord mesenchymal stem cells, the interference from red blood cells is an important factor affecting the quality and quantity of umbilical cord mesenchymal stem cells, because the existence of a large number of red blood cells limits the growth space of mesenchymal stem cells, and affects the viability of the stem cells, thereby having a great influence on the separation, extraction, exploitation and utilization of umbilical cord mesenchymal stem cells.

The present invention employs red blood cell lysis buffer to extract the umbilical cord mesenchymal stem cells, which can significantly mitigate the interference from red blood cells in the primary culture of umbilical cord mesenchymal stem cells. Specifically, the treatment with red blood cell lysis buffer used in the primary culture avoids the interference from red blood cells on the migration, adherence and proliferation of mesenchymal stem cells, ensures the successful separation of the mesenchymal stem cells, and improves cell purity, thereby meeting the requirements for the quantity of mesenchymal stem cells of clinical level, and further guaranteeing the viability of the stem cells as well. As a result, sufficient and viable mesenchymal stem cells are available for subsequent passage culture, cryopreservation and resuscitation, even clinical application, which is beneficial to the clinical conversion and application of the stem cells in the future.

In addition, the present invention combines the use of red blood cell lysis buffer with the serum-free culture medium, and ensures the successful extraction and high purity of umbilical cord mesenchymal stem cells, thus providing stable service for the storage and follow-up clinical application of umbilical cord mesenchymal stem cells. The culture medium is serum-free with a well defined composition, thereby avoiding instability of the cell growth during the culture due to batch difference of the serum, and also excluding the possibility of spreading xenogeneic pathogens.

Moreover, the method of the present invention is simple and easy to operate, which shortens the time for the primary culture.

Results of flow cytometry detection, viability determination, differentiation identification and pluripotency gene analysis have shown that the mesenchymal stem cells obtained by the method of present invention have high viability and purity, and strong differentiation capability, and the cell bank established with the stem cells can be directly utilized in scientific research and clinical adjuvant treatment.

BRIEF DESCRIPTION OF THE FIGURES

Now the implementations of the present invention will be described in detail in conjunction with accompanying drawings, in which:

FIG. 1 shows cell images during the screening of culture medium components, in which panel 1A shows cell morphology 48 hours after cells were inoculated in a medium comprising a low concentration of serum substitute, panel 1B shows cell morphology 24 hours after cells were inoculated in a medium comprising a high concentration of serum substitute, panel 1C shows cell morphology 24 hours after cells were inoculated in medium comprising a low concentration of bFGF, and panel 1D shows cell morphology after cells were passage cultured in a medium comprising a high concentration of bFGF.

FIG. 2 shows the cell morphology of the cultured umbilical cord mesenchymal stem cells, in which panel 2A shows the morphology of cells newly growing out of the tissue blocks, panel 2B shows the fibrous morphology of cultured cells after passage, and panel 2C shows the cell morphology of cells newly growing out without using red blood cell lysis buffer to separate mesenchymal stem cells.

FIG. 4 shows the analysis results of the cell viability and growth profile of the obtained umbilical cord mesenchymal stem cells by Vi-Cell cell vitality analyzer, in which panel 4A shows the real-time viability analysis of the umbilical cord mesenchymal stem cells, panel 4B shows the growth curve of the umbilical cord mesenchymal stem cells, and panel 4C shows the diameter distribution of the umbilical cord mesenchymal stem cells. The results indicated that the viability of the umbilical cord mesenchymal stem cells was above 99.7% with a diameter distribution of 9-15 μm, and the umbilical cord mesenchymal stem cells which appeared as spindle-shape and grew in whorls had a perfect roundness after digestion, and had proliferation profile characterized by latent stage, logarithmic growth stage and platform stage.

FIG. 5 shows the directed induced differentiation of the obtained umbilical cord mesenchymal stem cells into osteogenic cells, in which panel 5A shows dark red compounds produced by chromogenic reaction between alizarin red and calcium nodules during osteogenesis, panel 5B shows the differential expression of osteogenic marker gene OPN by the umbilical cord mesenchymal stem cells before and after differentiation, with Lane M: DNA molecular weight marker; Lane 1 and Lane 4: internal reference gene β-Actin; and Lane 2 and Lane 3: osteogenic marker gene OPN before and after induced differentiation.

FIG. 6 shows the directed induced differentiation of the mesenchymal stem cells into adipogenic cells, in which panel 6A shows the specific oil red O staining of the fat droplets in adipogenic cells, and panel 6B shows the differential expression of adipogenic marker gene PPAR-γ by the umbilical cord mesenchymal stem cells before and after differentiation, with Lane M: DNA molecular weight marker; Lane 2 and 4: internal reference gene β-Actin; and Lane 1 and 3: adipogenic marker gene PPAR-γ before and after induced differentiation.

FIG. 7 shows the RT-PCR analysis result of the pluripotency genes in the obtained umbilical cord mesenchymal stem cells at transcriptional level, with Lane M: DNA molecular weight marker; Lane 1: internal reference gene β-Actin; Lane 2: NANOG; Lane 3: OCT-4, Lane 4: SOX-2; and Lane 5: SSEA-4.

DETAILED DESCRIPTION OF PREFERRED EMBODIMENTS

Figure 3B:
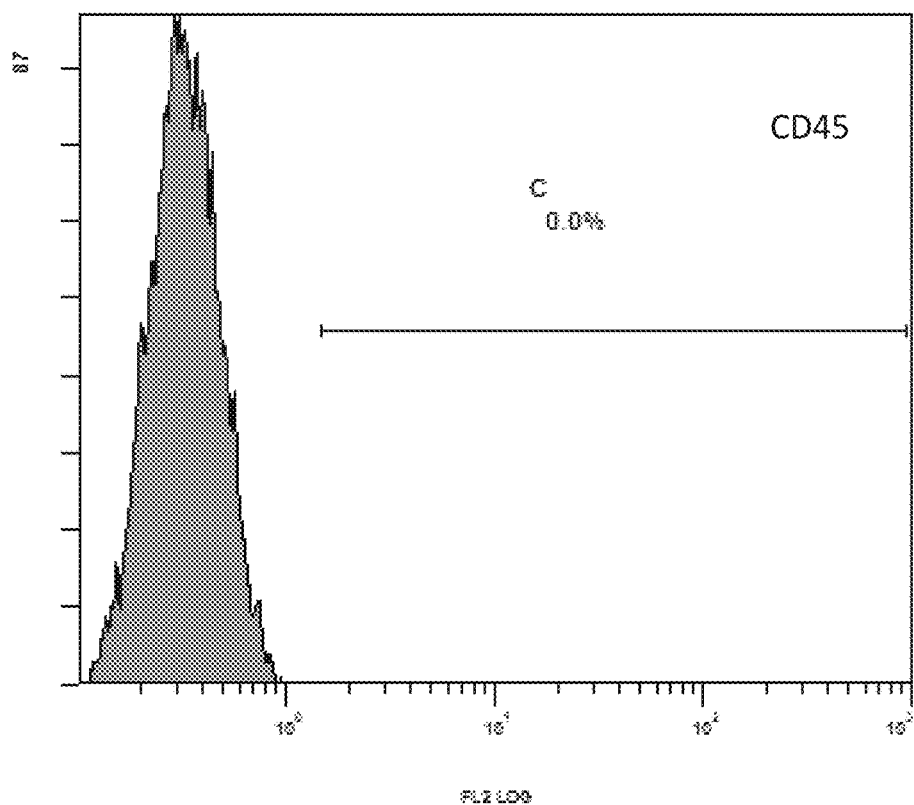
FIG. 3 (panels 3A to 3I) shows the analysis results of cell surface molecules of the obtained umbilical cord mesenchymal stem cells by flow cytometry, indicating that the umbilical cord mesenchymal stem cells expressed CD29, CD44, CD73, CD90, CD105 or HLA-ABC with ratio of positive cells greater than 99.0%, while did not express CD45, CD34 or HLA-DR with ratio of positive cells less than 1.0%.

The present invention will be further described in detail in conjunction with following embodiments, and the Examples are provided here only to elaborate the invention but not to be construed as limiting the scope of the invention.

The procedures without specified conditions shall be carried out in accordance with conventional conditions in the field the invention belongs to or recommended conditions by the supplier of the instruments and reagents; and the instruments or reagents without specified commercial sources are general products commercially available on the market.

Example 1 Screening of the Components of Serum-Free Medium for Mesenchymal Stem Cells (1) Screening of the Content of Serum Substitute Medium to be tested: 0.1 parts by volume of β-mercapto, 10 ng/ml recombinant human basic fibroblast growth factor (b-FGF, Peprotech), 1 part by volume of aqueous solution of non-essential amino acids (Catalog No. 11140, Gibco), 1, 2, 5, 8, 10, 12, 15, or 20 parts by volume of Knockout FBS serum substitute (Catalog No. 10828-028, Gibco), and 89 parts by volume of a-MEM.

In a biosafety cabinet, the third-passage hUC-MSCs separated from Wharton's jelly tissue of umbilical cord from a healthy neoborn by natural delivery were inoculated into a T75 cell culture flask at a density of $2 \times 10^4$ cells/cm$^2$, and 12-15 ml of medium commercially available were added as well to culture the cells. The cells were cultured till cells were observed to have completely adhered to walls of the flask, and the medium was replaced with 15 ml of medium to be tested. The growth of the cells was observed.

Results:

The cells proliferated slowly in the medium comprising 1, 2 or 5 parts by volume of serum substitute respectively, and 24 hours after inoculation, it was observed that part of the hUC-MSCs gathered while the cells were flat with poor refractive index and about 20% confluence; and subsequent observation 48 hours after inoculation showed that the hUC-MSCs were bright but the proliferation was almost stopped when 60% confluence was reached (see panel 1A). However, the cells grew well in the medium comprising 8, 10 or 12 parts by volume of serum substitute respectively, and 24 hours after inoculation, it was observed that the hUC-MSCs appeared as spindle-shape and gathered in whorls spreading much more, and the cells were bright, and 40-60% confluence was reached; and subsequent observation 48 hours after inoculation showed that the hUC-MSCs were bright and more than 90% confluence was reached. Similar to those in the low concentrations of serum substitute, the cells proliferated slowly in the medium comprising 15 or 20 parts by volume of serum substitute respectively, and the cells were flat with a clear outline (see panel 1B).

(2) Screening the Content of Recombinant Human Basic Fibroblast Growth Factor

Medium to be tested: 0.1 parts by volume of β-mercapto ethanol, 1, 2, 5, 8, 10, 12, 15, 18, or 20 ng/ml recombinant human basic fibroblast growth factor (b-FGF, Peprotech), 1 part by volume of aqueous solution of non-essential amino acids (Catalog No. 11140, Gibco), 10 parts by volume of Knockout FBS serum substitute (Catalog No. 10828-028, Gibco), and 89 parts by volume of a-MEM.

With reference to the method described in part (1) above, the stem cells from the same source were inoculated at the same density, and cultured in 12-15 ml medium commercially available. The cells were cultured till cells were observed to have completely adhered to walls of the flask, the medium was replaced with 15 ml of medium to be tested. The growth of the cells was observed.

Results:

The cells proliferated slowly in the medium comprising 1 or 2 ng/ml bFGF respectively, were in poor and undernourished state (see panel 1C). The cells grew normally in the medium comprising 5, 8, 10, 12 or 15 ng/ml bFGF respectively, and the cells were bright and in a good state. The cells grew well and were bright in the medium comprising 18 or 20 ng/ml bFGF respectively; however after several passages, the cells were prone to differentiate, and formed into clusters, or had tentacles stretched out (see panel 1D).

Example 2 Red Blood Cell Lysis Buffer Assisted Method of Extracting Umbilical Cord Mesenchymal Stem Cells Collecting and Transporting the Sample:

A umbilical cord tissue sample from a newborn by cesarean section delivery was collected aseptically, put into the preservation and transportion solution for umbilical cord comprising penicillin sodium, streptomycin sulfate, gentamicin and amphotericin B (the final concentration of each of penicillin sodium, streptomycin sulfate and gentamicin in D-Hank's was 150 U/ml respectively, while that of amphotericin B was 300 U/ml.), then transported in ice to a clean GMP cell laboratory within 2 hours.

Washing and Sterilizing the Sample:

In a biosafety cabinet, the fresh umbilical cord sample was placed in a 50 ml aseptic centrifuge tube, washed 2 times with 75% aqueous ethanol, then washed 3 times with sterile saline.

Pre-Processing the Umbilical Cord Sample:

The umbilical cord was cut into segments each of about 2-3 cm in length with ophthalmic scissors, the intravascular blood was removed with tweezers. Then each segment was longitudinally cut, two umbilical arteries and one umbilical vein were eliminated with hemostatic forceps, and the Wharton's jelly tissue was bluntly dissected and put into a 50 ml centrifuge tube. PBS with a volume of 2-5 times volume of the tissue was added, and the tissue was washed by shaking slightly.

Treating with the Red Blood Cell Lysis Buffer:

Wharton's jelly tissue was transferred to a clean and sterile culture dish and cut into tissue blocks each in size of 1-3 $mm^3$; the minced cord tissues were transferred into a centrifuge tube, and the red blood cell lysis buffer was added with a volume of 1.5-2 times the volume of the tissue blocks. The tissue blocks were treated with the buffer for 3 minutes at room temperature, the tissue blocks were collected by centrifugation at 1200 rpm, 4° C. for 6 minutes and the supernatant was discarded. The red blood cell lysis buffer comprised 5 g/L $NH_4Cl$ and 0.1 mM $Na_2$-EDTA, pH7.2-7.4.

Primary Culture:

The minced tissue blocks of Wharton's jelly tissue were plated evenly on 100 mm sterile culture dishes to reach a coverage of 70% respectively, the serum-free medium for mesenchymal stem cells with a volume of 4 times the volume of the blocks (about 10 ml) was added to each dish; then the dishes were transferred into an incubator at 37° C., 5% $CO_2$ for culture. The dishes were removed out of the incubator on the $3^{rd}$ day to supply 5 ml of fresh medium; and the tissue blocks were removed when cells have uniformly grown out of the bottom of the tissue blocks on the $7^{th}$ day (see panel 2A). 5 ml of PBS was added to each dish which was shaken gently for washing, then PBS was discarded; then 10 ml of fresh medium was added to each dish for further culture, during which the medium was replaced with fresh medium every 3 days. The serum-free medium for mesenchymal stem cells comprised 0.1 parts by volume of β-mercapto ethanol, 1 part by volume of aqueous solution of non-essential amino acids (Catalog No. 11140, Gibco), 10 parts by volume of Knockout™ serum substitute, 89 parts by volume of a-MEM/DMEM-F 12 and b-FGF at a final concentration of 10 ng/ml.

Cell Passage:

On the $12^{th}$ day after the tissue blocks were plated on the dishes, while about 50% confluence was reached, the cells were digested with trypsin at a mass faction of 0.125% for 1-2 minutes (the side walls of culture dishes or flasks were patted during the digestion), then the cells were collected by centrifugation at 1200 rpm, 4° C. for 6 minutes and the supernatant was discarded. The cells were inoculated in a T75 cell culture flask and cultured in the serum-free medium for mesenchymal stem cells till 80-90% confluence was reached, then the cells were collected for reserving or were further passage cultured. Panel 2B showed the fibrous morphology of cells cultured after passage.

Example 3 Red Blood Cell Lysis Buffer Assisted Method of Extracting Umbilical Cord Mesenchymal Stem Cells The red blood cell lysis buffer used in this Example comprised 10 g/L $NH_4Cl$ and 0.1 mM $Na_2$-EDTA, pH 7.2-7.4.

The process was carried out with reference to the method described in Example 2 above. The mesenchymal stem cells grew out of the bottom of the tissue blocks on the 5$^{th}$ day of culture, and formed cell-clusters in whorls around the 7$^{th}$ day of culture. After the removal of the tissue blocks and replacement with fresh medium, 60% confluence was reached around 12$^{th}$ day, and the cells were passaged after trypsin digestion. The purity of the cells after three passages was greater than 99% while the viability was more than 95%.

Example 4 Method of Extracting Mesenchymal Stem Cells without Using Red Blood Cell Lysis Buffer Collecting, transporting, pre-processing and the like of the cord tissue sample were performed with reference to those described in Example 2 above. The Wharton's jelly tissue was cut into minced tissue blocks each in size of 1-3 mm$^3$ and directly plated evenly on 100 mm sterile culture dishes to reach a coverage of 70% of the dish bottom without treatment with the red blood cell lysis buffer. 10 ml of serum-free medium for mesenchymal stem cells was added to each dish, and then the dishes were transferred into an incubator at 37° C., 5% CO$_2$ for culture. Cells grew out of the bottom of the tissue blocks on the 9$^{th}$ day; however, a large number of red blood cells adhered to the bottom of the dishes, occupying the area the stem cells should have adhered to (see panel 2C). Therefore, the stem cells had a weakened adherence to the walls and were in poor growth.

Example 5 Methods of Extracting Mesenchymal Stem Cells with Different Concentrations of Red Blood Cell Lysis Buffer Collecting, transporting, pre-processing and the like of the cord tissue sample were performed with reference to those described in Example 2 above. The Wharton's jelly tissue was cut into minced tissue blocks each in size of 1-3 mm$^3$, and red blood cell lysis buffer comprising 1, 2, 5, 7, 10, 15 or 20 g/L NH$_4$Cl and 0.1 mM Na$_2$-EDTA (pH 7.2-7.4) was added and treated the blocks for 2 minutes. The blocks were directly plated evenly on 100 mm sterile culture dishes to reach a coverage of 70% area of the dish bottom, and 10 ml of serum-free medium for mesenchymal stem cells was added to each dish, then the dishes were transferred into an incubator at 37° C., 5% CO$_2$. The growth of the cells was observed.

Results:

Upon treatment with red blood cell lysis buffer comprising 1 or 2 g/L NH$_4$Cl, there were still evident red blood cells on the bottom of the culture dishes, preventing the mesenchymal stem cells from adherence. Upon treatment with red blood cell lysis buffer comprising 5, 7 or 10 g/L NH$_4$Cl, there were few red blood cells on the dish bottom, and the mesenchymal stem cells grew out of the bottom of tissue blocks quite quickly (5-7 days). Upon treatment with red blood cell lysis buffer comprising 15 or 20 g/L NH$_4$Cl, there were no red blood cells observed on the dish bottom; however, it took much longer time for the mesenchymal stem cells growing out of the bottom of tissue blocks (7-12 days).

Example 6 Methods of Extracting Mesenchymal Stem Cells from Umbilical Cords with Different Duration of Treatment with Red Blood Cell Lysis Buffer Collecting, transporting, pre-processing and the like of the cord tissue sample were performed with reference to those described in Example 2 above. The Wharton's jelly tissue were cut into minced tissue blocks each in size of 1-3 mm$^3$, and red blood cell lysis buffer comprising 5 g/L NH$_4$Cl and 0.1 mM Na$_2$-EDTA (pH 7.2-7.4) was added and treated the cord tissue blocks for 1, 2, 5, 7 or 10 minutes respectively. Then the blocks were directly plated evenly on 100 mm sterile culture dishes to reach a coverage of 70% area of the dish bottom, and 10 ml of serum-free medium for mesenchymal stem cells was added to each dish, then the dishes were transferred into an incubator at 37° C., 5% CO$_2$. The growth of the cells was observed.

Results:

Upon treatment for 1 minute, there were still evident red blood cells on the bottom of the culture dishes, preventing the mesenchymal stem cells from adherence. Upon treatment for 2 or 5 minutes, there were few red blood cells on the dish bottom, and the mesenchymal stem cells grew out of the bottom of tissue blocks quite quickly (5-7 days). Upon treatment for 7 or 10 minutes, there were no red blood cells observed on the dish bottom; however, it took much longer time for the few mesenchymal stem cells growing out of the bottom of tissue blocks (7-12 days), and the new mesenchymal stem cells expanded very slowly.

Example 7 Morphological Identification of Umbilical Cord Mesenchymal Stem Cells By separation and culture as described in Example 2 above, individual umbilical cord mononuclear cells were observed on the 3$^{rd}$ day after block plating, and bright and adherent cells in round shape were visible under microscope. After 5 days of culture, those bright, adherent and round cells could be observed under microscope to have tentacles stretched out and adhered to the walls in spindle-shape. About 10 days, cell clusters growing in whorls appeared. During digestion and passage culture, the stem cells were in homogeneous morphology and proliferated rapidly, and state of the cells kept stable during passage.

Example 8 Analysis of Surface Markers of Umbilical Cord Mesenchymal Stem Cells by Flow Cytometry The third-passage cells separated and cultured in Example 3 grew to 90% confluence, and digested with 2 ml 0.125% trypsin. The cells were collected by centrifugation at 1200 rpm, 4° C. for 6 minutes and the supernatant was discarded. After washed 2 times with PBS, the cells were transferred to flow cytometry tubes with 1×10$^5$ cells in each tube. Then 5 μL of each of antibodies CD34-PE, CD45-FITC, CD29-FITC, CD44-PE, CD73-PE, CD105-PE, CD90-FITC, HLA-ABC-FITC, HLA-DR-PE, IgG1-PE (isotype control) and IgG1-FITC (isotype control) was added into the tubes respectively, mixed and incubated in dark at 4° C. for 30 minutes. Afterwards, the cells were washed once with PBS, the supernatant was discarded by centrifugation, and the cells were re-suspended and mixed evenly in 500 μl of PBS, and then detected on a flow cytometer (Flow Cytometer XL, Beckman), with 1×10$^4$ cells collected for each sample.

Figure 3C:
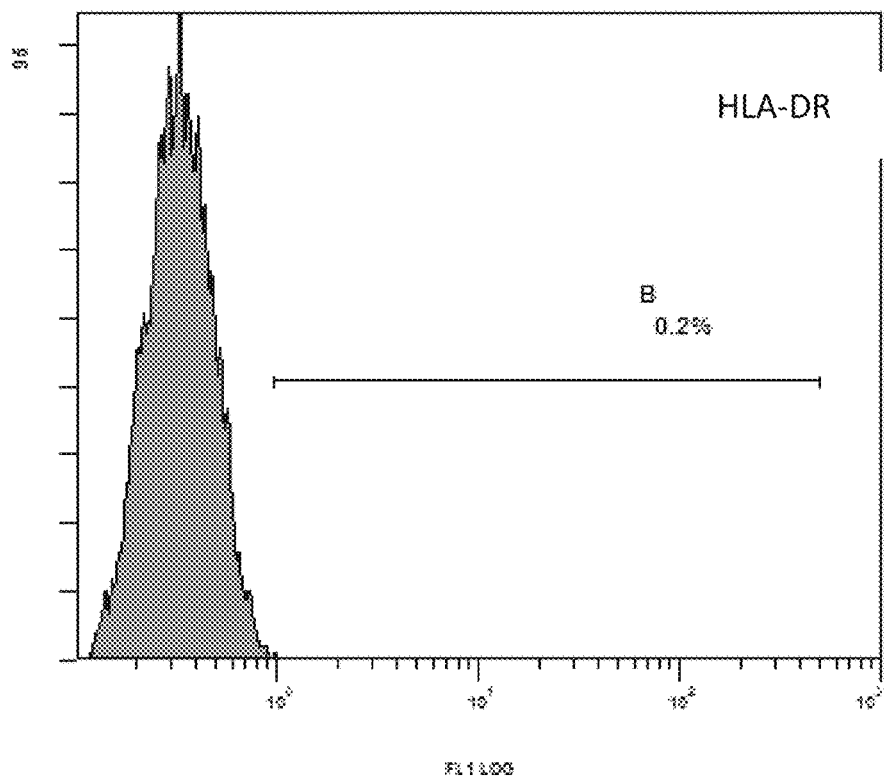
Figure 3D:
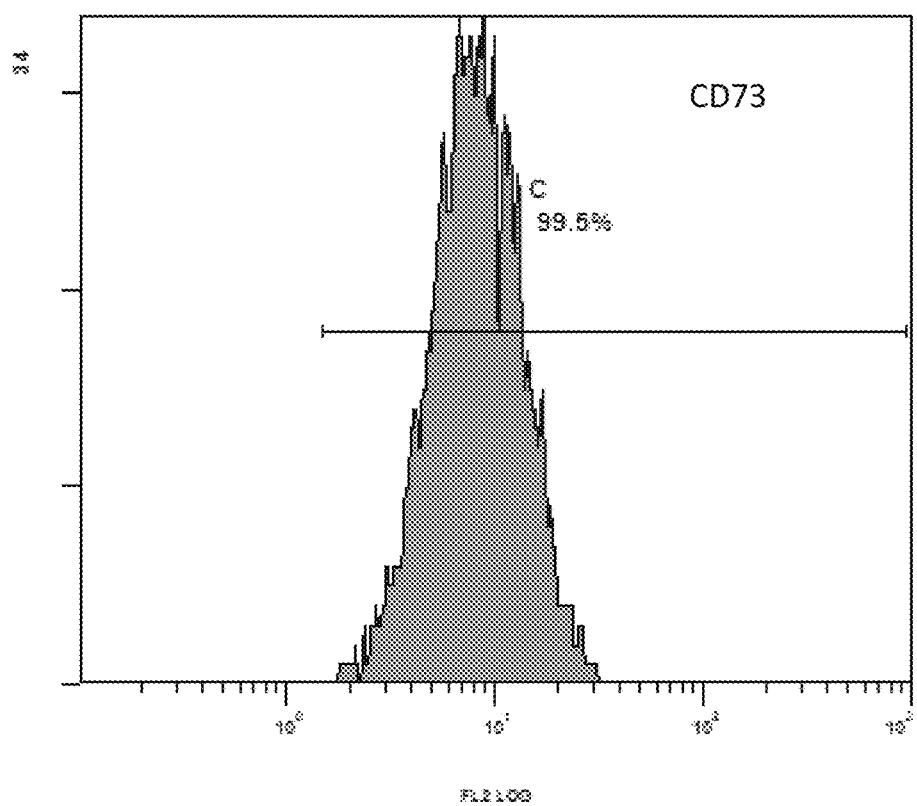
Figure 3E:
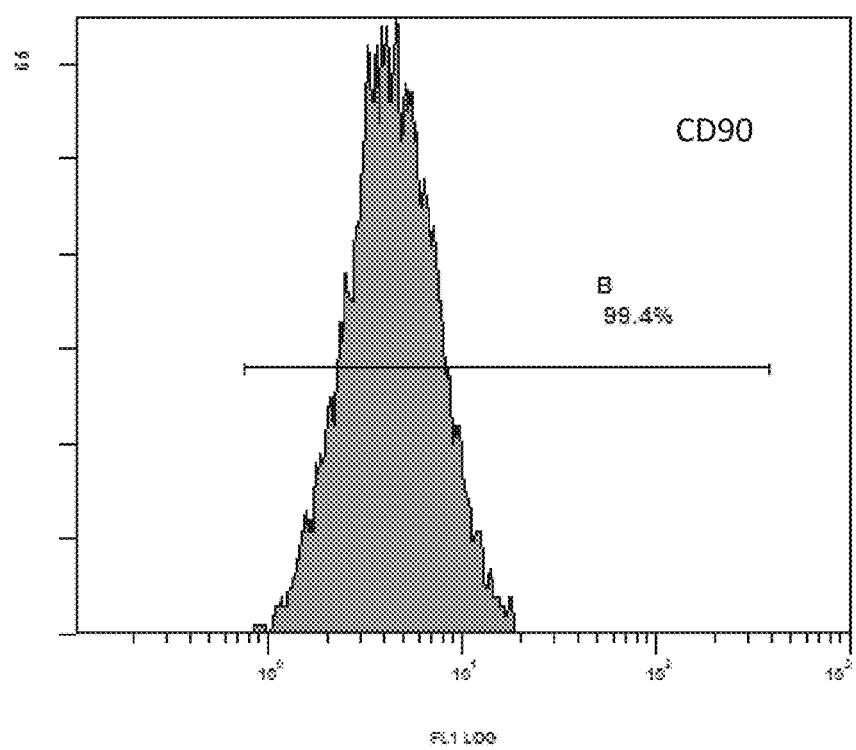
Figure 3F:
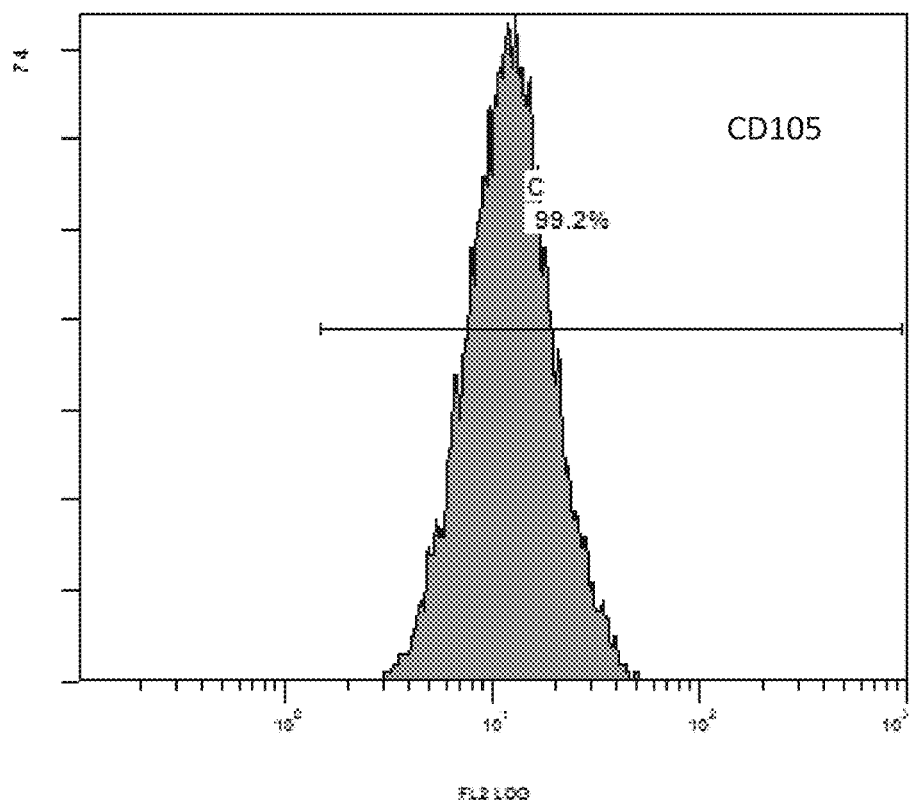
Figure 3G:
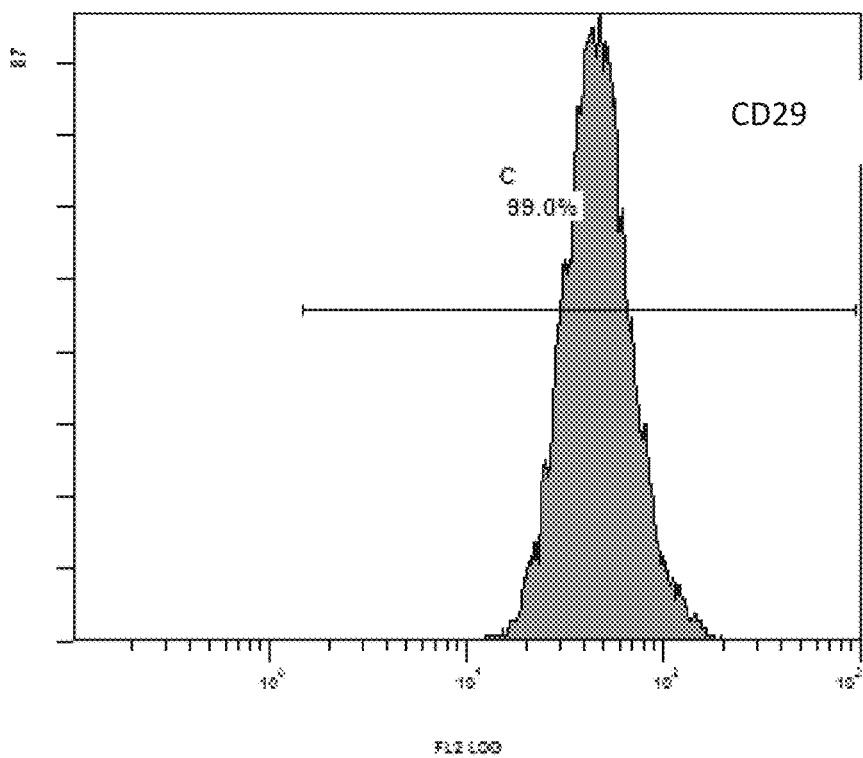
Figure 3H:
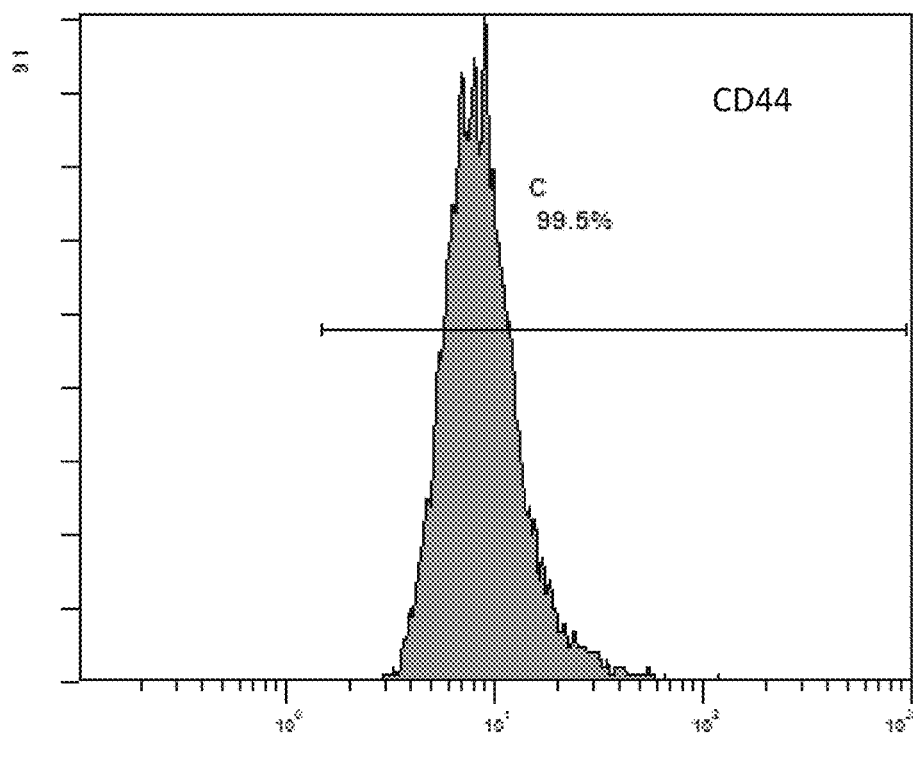
Figure 3I:
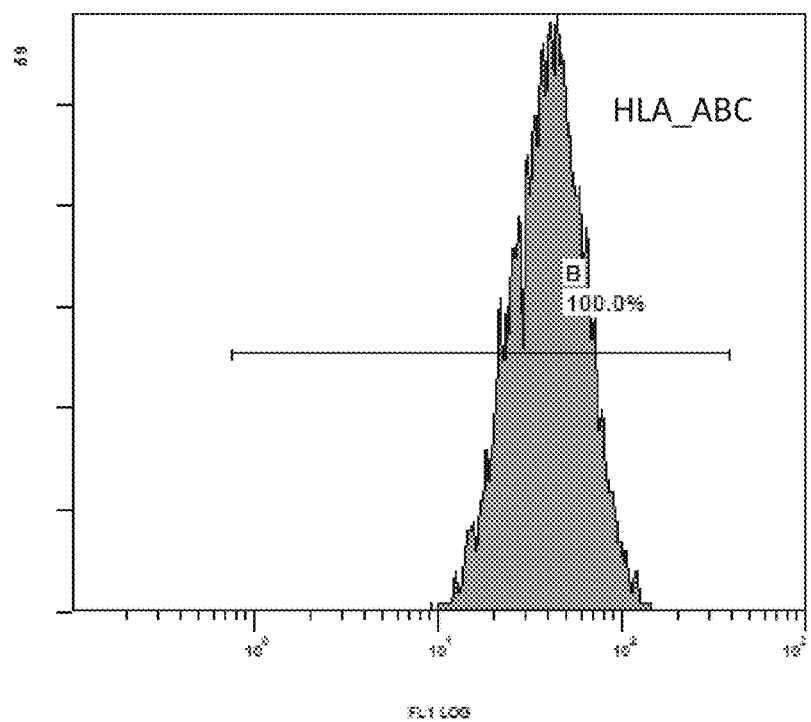

The immunophenotypes of the cells were as follows:
Ratio of positive cells: CD29>99.0%, CD44>99.0%, CD73>99.0%, CD105>99.0%, CD90>99.0%, and HLA-ABC 99.0%;
Ratio of positive cells: CD34<1.0%, CD45<1.0%, and HLA-DR<1.0%.
Results are provided in FIG. 3.

Example 9 Analysis of Cell Viability and Growth Profile of the Umbilical Cord Mesenchymal Stem Cells by Cell Viability Analyzer The second-passage cells separated and cultured in Example 2 were inoculated into a T25 culture flask. The cells grew to 90%-100% confluence, and were digested with 2 ml 0.125% trypsin. Then the cells were collected and inoculated to two 6-well plates at a density of $1 \times 10^5$ cells per well. After all the cells had adhered and grown for 10 hours, cells in two wells were collected and prepared into a cell suspension in 500 µl of PBS which was then analyzed on a cell viability analyzer (Cell Viability Analyzer Vi-Cell XR, Beckman). Then, sampling analyzing were performed every 12 hours, and growth curve was drawn accordingly.

Results (see FIG. 4) showed that the viability of the umbilical cord mesenchymal stem cells was above 99.7% with a diameter distribution of 9-12 µm. The umbilical cord mesenchymal stem cells which appeared as spindle-shape and grew in whorlshad a perfect roundness after digestion, and a proliferation profile characterized by latent stage, logarithmic growth stage and platform stage.

Example 10 Identification of Multi-Directional Differentiation Potential of Umbilical Cord Mesenchymal Stem Cells Osteogenic Differentiation The fourth-passage umbilical cord pluripotent stem cells separated and cultured in Example 2 were inoculated to a 6-well cell culture plate at a density of $3 \times 10^4$ cells/cm². After 24 hours, 2 ml of freshly prepared human UC MSC osteogenic differentiation medium (HUXUC-90021, Cyagen) was added to each well, and the medium was replaced with fresh osteogenic differentiation medium every 3 days. After 2 weeks, the cells were fixed with paraformaldehyde, and stained with alizarin red for 3-5 minutes. At the same time, RT-PCR was performed to identify the expression level of osteogenic marker gene OPN at transcriptional level.

Results (see FIG. 5) showed that alizarin red reacted with calcium nodules during osteogenesis to give a dark red color, after two weeks of osteogenic induction of the umbilical cord mesenchymal stem cells obtained by the method of present invention; furthermore, the osteogenic marker gene OPN also showed differential expression level before and after induction.

Adipogenic Differentiation

The fourth-passage umbilical cord pluripotent stem cells separated and cultured in Example 3 were inoculated to a 6-well cell culture plate at a density of $2 \times 10^4$ cells/cm². When 100% confluence had reached, fresh adipogenic differentiation medium A solution (HUXUC-90031, Cyagen) was added to each well to start induction; after 3 days, the medium was replaced with adipogenic differentiation medium B solution and the culture was maintained for 24 hours. The medium replacement happened in such a cycle. When more but fairly small fat droplets appeared, the culture system was maintained with adipogenic differentiation medium B solution for 7 days; and after induction, the cells were fixed with 4% paraformaldehyde and stained with oil red O. At the same time, RT-PCR was performed to identify adipogenic marker gene PPAR-γ at transcriptional level.

Results (see FIG. 6) showed that oil red O staining of adipogenic cells were obvious after two weeks of adipogenic induction of the hUC-MSCs obtained by the method of present invention. Furthermore, the adipogenic marker gene PPAR-γ also showed differential expression level before and after induction.

Example 11 RT-PCR Analysis of Pluripotency Genes of the Umbilical Cord Mesenchymal Stem Cells The third-passage umbilical cord pluripotent stem cells separated and cultured in Example 2 were inoculated to a T25 cell culture flask at a density of $5 \times 10$ cells/cm². 2-3 days later when 100% confluence had reached, RNA was extracted, and the extracted RNA was reverse transcribed to obtain cDNA sample which was then amplified by PCR. Then agarose gel electrophoresis was performed, and the results were observed by electrophoresis gel imager.

Results (see FIG. 7) showed that umbilical cord pluripotency marker genes NANOG, OCT4, SOX2 and SSEA4 had corresponding bands in different degrees of brightness.

The above description of the specific implementations of the present invention is not to be construed as limiting the scope of the invention. The skilled person in this field can make various changes or deformations according to the present invention. As long as not departing from the spirit of the present invention, those changes or deformations are within the scope of the claims attached to the present invention.

What claimed is:

1. A method for separating and culturing umbilical cord mesenchymal stem cells, the method comprising:
    treating Wharton's jelly tissue separated from umbilical cord utilizing a red blood cell lysis buffer to obtain mesenchymal stem cells, and
    culturing the mesenchymal stem cells utilizing a serum-free medium for mesenchymal stem cells;
    wherein the red blood cell lysis buffer is an aqueous solution comprising 1-20 g/L NH$_4$Cl and 0.05-0.2 mM Na2-EDTA;
    wherein the serum-free medium for mesenchymal stem cells consists of 0.05-0.2 parts by volume of β-mercapto ethanol, 0.5-2 parts by volume of an aqueous solution of non-essential amino acids, 8-12 parts by volume of a serum substitute, 85-95 parts by volume of a-MEM or DMEM-F12, and recombinant human basic fibroblast growth factor at a final concentration of 5-15 ng/ml, and
    wherein the aqueous solution of non-essential amino acids comprises glycine, alanine. L-asparagine, L-aspartic acid, glutamic acid, proline and serine each at a concentration of 8-12 mM.

2. The method according to claim 1, wherein the red blood cell lysis buffer is an aqueous solution comprising 5-10 g/L NH$_4$Cl and 0.1 mM Na$_2$-EDTA, pH 7.2-7.4.

3. The method according to claim 1, wherein the serum-free medium for mesenchymal stem cells consists of 0.1 parts by volume of β-mercapto ethanol, 1 part by volume of the aqueous solution of non-essential amino acids, 10 parts by volume of the serum substitute, 89 parts by volume of a-MEM or DMEM-F12 and the recombinant human basic fibroblast growth factor at a final concentration of 10 ng/ml.

4. The method according to claim 1, wherein the treating and the culturing comprise: cutting an obtained Wharton's jelly tissue into tissue blocks, adding the red blood cell lysis buffer with a volume of 1-3 times the volume of the tissue blocks, and treating the tissue blocks with the red blood cell lysis buffer at room temperature for 2-5 minutes; and, culturing obtained tissue blocks with the serum free medium for mesenchymal stem cells to obtain primary mesenchymal stem cells.

5. The method according to claim 1, wherein the treating and the culturing comprise the following steps:
(1) Pretreatment of umbilical cord tissue:
cutting fresh umbilical cord into segments, removing intravascular blood, longitudinally cutting each segment, eliminating umbilical artery and umbilical vein, bluntly dissecting the Wharton's jelly tissue and washing the same with PBS;
(2) Treatment with the red blood cell lysis buffer:
cutting the Wharton's jelly tissue obtained by step (1) into tissue blocks, adding the red blood cell lysis buffer to treat the tissue blocks, collecting treated tissue blocks by centrifugation, and washing them with PBS; and
(3) Primary culture:
culturing the tissue blocks obtained by step (2) in the serum-free medium for mesenchymal stem cells to obtain primary mesenchymal stem cells.

6. The method according to claim 5, wherein the step (1) includes: cutting the fresh umbilical cord into segments each of 2-3 cm in length, removing the intravascular blood, longitudinally cutting each segment, eliminating the umbilical artery and the umbilical vein, bluntly dissecting the Wharton's jelly tissue, adding PBS with a volume of 2-5 times the volume of the tissue, and washing the tissue by shaking.

7. The method according to claim 5, wherein prior to the step (1), the method further comprises washing, preserving and pre-processing the umbilical cord.

8. The method according to claim 5, wherein the method further comprises the following steps:
(4) Supernatant Detection:
taking supernatant of cell culture obtained by step (3) and detecting one or more selected from the group consisting of hepatitis A, hepatitis B, hepatitis C, syphilis, human immunodeficiency virus, mycoplasma, chlamydia and endotoxin;
(5) Passage Culture:
selecting cultured cells with negative results in step (4), collecting cells by centrifugation after trypsin digestion, passage culturing, and collecting the cells for reserving or freezing conservation, or continuing passage culture; and
(6) Cell Detection:
taking the cells cultured in step (5), and detecting one or more selected from the group consisting of differentiation, cell activity, cell purity, cell contamination and proliferation profile.

9. The method according to claim 8,
wherein the step (2) includes: cutting washed Wharton's jelly tissue into tissue blocks each in size of 1-3 mm$^3$ adding the red blood cell lysis buffer with a volume of 1.5-2 times the volume of the tissue blocks, treating the tissue blocks with the buffer at room temperature for 2-5 minutes, collecting treated tissue, blocks by centrifugation, and washing 2-3 times with PBS;
wherein the step (3) includes: plating the tissue blocks obtained by step (2) evenly on a culture dish to reach a coverage of 60-80 %, adding the serum-free medium for mesenchymal stem cells with a volume of 3-5 times the volume of the tissue blocks, then culturing at 37° C., 5% $CO_2$ for 3-5 days, during which culture period half of the medium is replaced with fresh serum-free medium for mesenchymal stem cells removing the tissue blocks when cells have evenly grown out of bottom of the tissue blocks at 5-15 days, at which time the medium is removed in its entirety and replaced with fresh serum-free medium for mesenchymal cells; and further culturing the cells in the culture dish, during which the medium is replaced with fresh serum-free medium for mesenchymal stem cells every 3-4 days;
wherein the step (4) includes: taking supernatant of cell culture obtained by step (3) and detecting all of the followings: hepatitis A, hepatitis B, hepatitis C, syphilis, human immunodeficiency virus, mycoplasma, chlamydia and endotoxin; and
wherein the step (5) includes: selecting cultured cells with all negative results in step (4), performing trypsin digestion at 30-80%, collecting cells by centrifugation, passage culturing the cells in serum-free medium for mesenchymal stem cells to reach 50-90% confluence, and collecting the cells for reserving or freezing conservation, or continuing passage culture.

10. The method according to claim 9, wherein the trypsin is utilized at a mass percent concentration of 0.125%, and the digestion is performed for 1-2 minutes while patting side walls of culture dish or culture flask utilized.

11. The method according to claim 9, wherein the collecting of the cells for reserving or freezing conservation comprises freezing the cells in liquid nitrogen at −196° C. at a density of 2-3×10$^6$ cells/ml.

12. The method according to claim 8, wherein the step (6) includes: taking the cells cultured in step (5), and detecting all of the followings: differentiation, cell activity, cell purity, cell contamination and proliferation profile.

13. The method according to claim 7, wherein the steps of washing, preserving and pre-processing the umbilical cord comprises: collecting aseptically umbilical cord tissue from a healthy newborn by natural or cesarean section delivery, surface washing the umbilical cord with sterile saline, putting the umbilical cord tissue into preservation and transportation solution; and before usage, washing fresh umbilical cord 2-3 times with 75% aqueous ethanol, then 3-5 times with sterile saline.

14. The method according to claim 13, wherein the preservation and transportation solution for umbilical cord is magnesium and calcium free D-Hank's Buffered Saline Solution comprising penicillin sodium, streptomycin sulfate, gentamicin and amphotericin B for injection.

15. The method according to claim 1, wherein the method comprises:
cutting washed Wharton's jelly tissue of umbilical cord into tissue blocks each in size of 1-3 mm$^3$;
adding the red blood cell lysis buffer with a volume of 1.5-2 times the volume of the tissue blocks;
treating the tissue blocks with the buffer at room temperature for 2-5 minutes;
plating obtained tissue blocks evenly on a culture dish to reach a coverage of 60-80 %;
adding the serum-free, medium for mesenchymal stem cells with a volume of 3-5 times the volume of the tissue blocks;
culturing at 37° C., 5% $CO_2$ for 3-5 days, during which culture period half of the medium is replaced with fresh serum-free medium for mesenchymal stem cells removing the tissue blocks when cells have uniformly grown out of bottom of the tissue blocks a 5-15 days, at which time the medium is removed in its entirety and replaced with fresh serum-free medium for mesenchymal stem cells; and further culturing the cells in the culture dish, during which the serum-free medium is replaced with fresh serum-free medium for mesenchymal stem cells every 3-4 days.

16. A kit for separating and culturing mesenchymal stem cells, wherein the kit comprises a red blood cell lysis buffer and a serum-free medium for mesenchymal stem cells;
wherein the red blood cell lysis buffer is an aqueous solution comprising 1-20 g/L $NH_4Cl$ and 0.05-0.2 mM Na2-EDTA;
wherein the serum-free medium for mesenchymal stem cells consists of 0.05-0.2 parts by volume of β-mercapto ethanol, 0.5-2 parts by volume of an aqueous solution of non-essential amino acids, 8-12 parts by volume of a serum substitute, 85-95 parts by volume of a-MEM or DMEM-F12 and recombinant human basic fibroblast growth factor at a final concentration of 5-15 ng/ml, and
wherein the aqueous solution of non-essential amino acids comprises glycine, alanine, L-asparagine, L-aspartic acid, glutamic acid, proline and serine each at a concentration of 8-12 mM.

17. The kit according to claim 16, wherein the red blood cell lysis buffer is an aqueous solution comprising 5-10 g/L $NH_4Cl$ and 0.1 mM Na2-EDTA, pH 7.2-7.4.

18. The kit according to claim 16, wherein the serum-free medium for mesenchymal stem cells consists of 0.1 parts by volume of β-mercapto ethanol, 1 part by volume of the aqueous solution of non-essential amino acids, 10 parts by volume of the serum substitute, 89 parts by volume of a-MEM or DMEM-F12 and the recombinant human basic fibroblast growth factor at a final concentration of 10 ng/ml.

* * * * *